(12) United States Patent
Billard (10) Patent No.: US 10,595,752 B2
(45) Date of Patent: Mar. 24, 2020

(54) DIAGNOSTIC PROBE FOR MEASURING THE DEFORMATION OF AN INTERNAL CAVITY

(71) Applicant: AKSE, Moissy-Cramayel (FR)

(72) Inventor: Georges Billard, Perols (FR)

(73) Assignee: AKSE, Moissy-Cramayel (FR)

( * ) Notice: Subject to any disclaimer, the term of this patent is extended or adjusted under 35 U.S.C. 154(b) by 63 days.

(21) Appl. No.: 15/575,950

(22) PCT Filed: May 20, 2016

(86) PCT No.: PCT/FR2016/051200
§ 371 (c)(1),
(2) Date: Nov. 21, 2017

(87) PCT Pub. No.: WO2016/185147
PCT Pub. Date: Nov. 24, 2016

(65) Prior Publication Data
US 2018/0146892 A1    May 31, 2018

(30) Foreign Application Priority Data

May 21, 2015 (FR) .................................. 15 01063

(51) Int. Cl.
*A61B 5/20* (2006.01)
*A61B 5/11* (2006.01)
(Continued)

(52) U.S. Cl.
CPC .......... *A61B 5/1126* (2013.01); *A61B 5/0492* (2013.01); *A61B 5/04882* (2013.01);
(Continued)

(58) Field of Classification Search
CPC ........... A61B 5/202; A61B 5/227; A61B 5/43; A61B 5/4306; A61B 5/4337; A61B 5/4375; A61B 5/4393; A61B 2562/0247
See application file for complete search history.

(56) References Cited

U.S. PATENT DOCUMENTS 3,643,651 A * 2/1972 Cuadros ............... A61B 5/1076
600/591
2002/0193670 A1* 12/2002 Garfield ............... A61B 5/0444
600/304

(Continued)

FOREIGN PATENT DOCUMENTS

| EP | 1 600 103 A1 | 11/2005 |
| FR | 2941860 A1 | 8/2010 |
| WO | 2013 116310 A1 | 8/2013 |

*Primary Examiner* — Puya Agahi
(74) *Attorney, Agent, or Firm* — Craft Chu PLLC; Andrew W. Chu (57) ABSTRACT

The diagnostic probe can be inserted into a vaginal or rectal body endo-cavity of the human body so as to measure the displacement of the walls of the endo-cavity and organs that surround the endo-cavity and so as to measure the displacement and the passive and active resistance of at least one muscle of the perineum. The diagnostic probe includes at least one endo-cavitary body provided with at least two pressure sensors arranged in the same plane and acting either in the same direction or in two opposite directions. The endo-cavitary body can be deformable without opposing resistance and matching the walls of the endo-cavity. The endo-cavitary body includes at least one device for measuring the displacement of the endo-cavitary wall along the three axes X, Y and Z.

10 Claims, 2 Drawing Sheets (51) Int. Cl.
*A61B 5/00* (2006.01)
*A61B 5/22* (2006.01)
*A61B 5/0488* (2006.01)
*A61B 5/0492* (2006.01)

(52) U.S. Cl.
CPC ............... *A61B 5/11* (2013.01); *A61B 5/202* (2013.01); *A61B 5/227* (2013.01); *A61B 5/4337* (2013.01); *A61B 5/43* (2013.01); *A61B 5/4306* (2013.01); *A61B 5/4375* (2013.01); *A61B 5/4393* (2013.01); *A61B 2562/0247* (2013.01); *A61B 2562/063* (2013.01); *A61B 2562/164* (2013.01)

(56) References Cited

U.S. PATENT DOCUMENTS

| | | | |
|---|---|---|---|
| 2004/0030360 A1 | 2/2004 | Eini | |
| 2007/0293792 A1 | 12/2007 | Sliwa | |
| 2015/0032032 A1* | 1/2015 | Egorov | ............... A61B 5/4337 600/591 |
| 2015/0112230 A1 | 4/2015 | Iglesias | |

* cited by examiner

DIAGNOSTIC PROBE FOR MEASURING THE DEFORMATION OF AN INTERNAL CAVITY

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention is related to the paramedical and medical field and more particularly to the analysis of the functional state of the anatomical structures involved in the urinary and/or fecal continence and incontinence mechanism.

For example, but non-restrictively, this analysis can be carried out in pre- or post-partum to observe the functional consequences of an obstetric trauma.

Indeed, after such a trauma, namely a normal vaginal delivery, determined perineal and/or sphincter pathologies can develop and cause disorders, namely urinary, anorectal and/or sexual disorders, which can be distressing, even disabling, for the patient.

Therefore, it is necessary, in a first stage, to proceed to a diagnosis of the functional state of the muscles of the perineum of the female (or male) patient in order to propose her/him, in a second stage, adapted and specific re-education sessions or a surgical treatment depending on the results that have previously been obtained.

In general, incontinence is due to an increase in intra-abdominal pressure to which the urethral and/or anal canal closing muscles respond in a too slow and/or too weak and/or poorly coordinated way.

Now, the urethral and/or anal canal closing muscles include several groups of muscles.

A first group of muscles groups the urethral and anal sphincters, which are muscles that surround and lock the urethra and anal canal, respectively.

A second group of muscles groups the pubo-vaginal and pubo-rectal muscles, which tie the vagina and the anal canal, these muscles participate in the closing of the urethra and the anal canal by performing an antero-posterior mechanical deformation of the vagina and the anal canal.

The third group of muscles groups the muscles of the perineum in the form of a dome and which surround the lower end of the vagina and the anal canal, the muscles of the perineum participate in the locking of the urethra and/or the anal canal by damping by deformation the increased intra-abdominal pressure. In addition, the muscles of the perineum support the organs, which are located in the abdomen, for example, the bladder, the urethra, the vagina and the uterus for a woman, the prostate for a man, and the rectum.

Further factors also contribute to the dampening of the increase in intra-abdominal pressure, such as the mass of fat contained in the ischio-rectal fossa as well as the ligaments holding the organs inside the abdominal cavity.

It should be noted that these ligaments have a low deformation capacity. Thus, during a mechanical deformation, their strength is particularly important as the force and the speed of the mechanical deformation applied to them are high.

2. Description of Related Art Including Information Disclosed Under 37 CFR 1.97 and 37 CFR 1.98

Currently, in order to proceed to a functional analysis of the anatomical structures related to the incontinence mechanism, a practitioner, for example a physician or a physiotherapist, manually performs a functional analysis of a patient's perineum only.

The practitioner must then feel the result of the contraction of the perineum, which is initiated by the patient, appreciate its quality and then verbalize the control understood by the patient, so that she modifies in response the contraction of her perineum.

Such practices unfortunately provide no regularity, because they are very dependent on the practitioner and his experience and are limited to the functional analysis of the perineum, which is only one of the anatomical structures involved in the of continence and incontinence mechanism.

In order to try to cope with the drawbacks of the manual methods, the patent document FR 2 941 860, filed by the Applicant itself, discloses an instrument for measuring the various functional and organic parameters of the pelvic floor, i.e. of the muscles of the perineum.

This instrument comprises at least two rotationally hinged arms so as to pass from a closed position to an open position, and vice versa, thus reproducing the fingers of the practitioner, said instrument further comprising means for magnetically controlling of the spread angle of the arms.

In the interest of a diagnosis, the instrument disclosed in this document permits to determine the origin of the dysfunctions affecting the perineal-sphincter muscles by demonstrating, in particular, a functional deficit of the different types of muscle fibers (tonic and phasic fibers), a delayed triggering of the myotatic perineal locking reflex, a fibrosis of the muscle tissue, a neurological impairment, or also a distension of the connective tissue.

However, although it is very efficient and already brings about a substantial improvement over what already existed in the state of the art, this device can be further improved.

In particular, in view of the complexity of the incontinence mechanism described above, said device does not provide the possibility of measuring determined parameters such as the deformation and the displacement of the vaginal and/or rectal cavity due to the increase in intra-abdominal pressure and/or to the response by the pubo-vaginal and/or pubo-rectal muscles.

Now, the measurement of all the parameters involved in the incontinence mechanism would permit an accurate diagnosis of the cause of incontinence and in particular of one of the main causes of urethral and perineal hypermobility. This measurement would allow to accurately define the level of displacement of the organs and the level of intra-abdominal pressure at which the urinary or anal leaks occur.

In the state of the art, the MRI permits to measure the displacement of the organs, but does not permit to establish a correlation between the pressures, the displacements and the leakage.

Now, the establishment of an accurate diagnosis would permit to perfectly define the indications for surgery or re-education and to optimize the exercises, which are then proposed to the female, or male, patient, with a view to re-educating the perineal function.

BRIEF SUMMARY OF THE INVENTION

The invention thus provides the possibility of coping with the various drawbacks of the state of the art by providing a probe permitting to measure, in response to an increase in intra-abdominal pressure, the displacement and the mechanical deformation of the perineum and of the vaginal or rectal cavity induced, for example, by a cough, as well as the behavior of the urethral or anal cavity closing muscles and the starting point of a urinary leakage with respect to the levels of pressure and deformation.

To this end, the present invention relates to a diagnostic probe designed capable of being inserted into a body, vaginal or rectal endo-cavity of the human body and of permitting to at least measure the displacement of the walls of said endo-cavity and of the surrounding organs as well as to measure the displacement and the passive and active resistance of at least one muscle of the perineum, the diagnostic probe including at least one endo-cavitary body equipped with at least two pressure measuring sensors arranged in the same plane and acting either in the same direction or in two opposite directions, wherein the endo-cavitary body is designed capable of being deformable without opposing resistance and of matching the walls of said endo-cavity, the endo-cavitary body including at least one means for measuring the displacement of the endo-cavitary wall along the three axes X, Y and Z, said means for measuring the displacement being connected to at least one spatial reference element X, Y, Z.

Advantageously, these features permit to measure the displacement and the deformation of the endo-cavity, which the diagnostic probe is inserted into. In this way, it is possible to obtain data related to the behavior of the anatomical structures surrounding the endo-cavity after an increase in intra-abdominal pressure.

In addition, the diagnostic probe cooperates with means for analyzing the pressure/displacement measurements performed and for reconstructing a dynamic three-dimensional view of the displacement of said endo-cavity.

This feature permits to accurately model the displacement and the deformation of the endo-cavity after an increase in the intra-abdominal pressure and thus to replace an expensive and much less complete examination that would be performed using a magnetic resonance imagery or "MRI".

According to a peculiarity of the invention, the endo-cavitary body is formed by a flexible strip folded in half so as to match, in a sagittal plane, the walls of said endo-cavity, the endo-cavitary body including two ends each connected to an ex-vivo base of the diagnostic probe, the ex-vivo base being arranged at the opening of the endo-cavity and including a biocompatible adhesive means for reinforcing the maintaining in position of said probe.

The flexibility of the endo-cavitary body permits to avoid that during an examination the diagnostic probe is expelled from the endo-cavity by a loosening of an organ or "prolapse" of one of the organs surrounding the endo-cavity, which the probe is inserted into.

In addition, in order to determine the moment at which the urine leakage occurs due to an increase in intra-abdominal pressure, the ex-vivo base includes at least one urine detector.

According to a particular embodiment of the invention, the means for measuring the displacement of the endo-cavitary wall consists of an inertial unit.

In order to obtain accurate measurements of the displacement and the deformation of the endo-cavity, which the diagnostic probe is inserted into, the spatial reference element X, Y, Z includes at least two means for measuring the displacement of the tendon unit of the perineum and the sacrum.

According to an additional feature of the invention, the diagnostic probe cooperates with at least two electrodes for measuring an electromyographic signal arranged on the abdomen of a male (or female) patient so as to record the abdominal electromyographic activity causing the intra-abdominal pressures.

The cooperation between the diagnostic probe according to the invention and the electromyographic electrodes permits to carry out a monitoring of the deformations and displacements of the endo-cavity, which the diagnostic probe is inserted into throughout the examination according to a time scale. Thus, it is possible to accurately determine the moment at which the urinary leakage occurs and the anatomical structure that is responsible for same.

In order to measure the displacement and the deformation of the walls of the endo-cavity at different levels of depth, the endo-cavitary body includes four means for measuring the displacement of the endo-cavitary wall.

This feature permits to indirectly measure the displacement and the deformation of the anatomical structures surrounding the endo-cavity, which the diagnostic probe is inserted into.

In the same way, in order to measure the level of resistance at which the urinary leakage occurs, the endo-cavitary body includes six pressure sensors. These pressure sensors are distributed pairwise along the endo-cavitary body and permit to measure the antero-posterior pressures that are applied to the walls of the endo-cavity at three different levels of depth.

For reasons of hygiene, when the probe is inserted into an endo-cavity, it cooperates with a sheath made of biocompatible polymeric material covering the endo-cavitary body.

The present invention includes many advantages. On the one hand, the probe according to the invention permits to measure, along the 3 axes X, Y and Z, deformations and the passive and active resistance of the anatomical structures responsible for continence and incontinence. On the other hand, in correlation with the antero-posterior pressure the endo-cavity, which the probe is inserted into, is submitted to, the time at which the leak occurs, and the onset of the increase in intra-abdominal pressure, it is possible to accurately identify the moment at which the leak takes place, the level of resistance at which the leakage takes place, and the anatomical structure that causes the incontinence.

Moreover, by means of the present probe, the diagnosis can be established under the physiological conditions in which the discomforts related to the continence disorders, i.e. in the vertical position, are likely to occur when the patient is standing. The discomforts as evoked may namely consist of urinary leaks.

Another advantage of the invention lies in that the present probe permits to establish a diagnosis independently from the operator, who handles said probe. Therefore, irrespective of the practitioner's experience, the established diagnosis will be extremely reliable.

Figure 1:
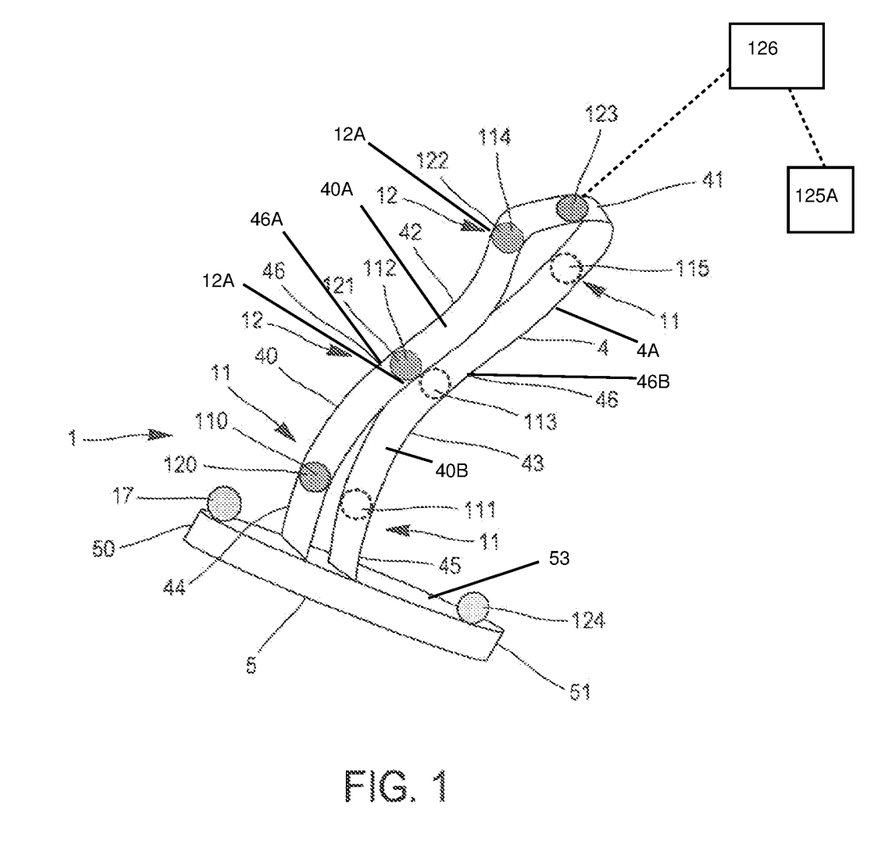
FIG. 1 is a perspective view of a diagnostic probe according to an embodiment according to the invention.
Figure 2:
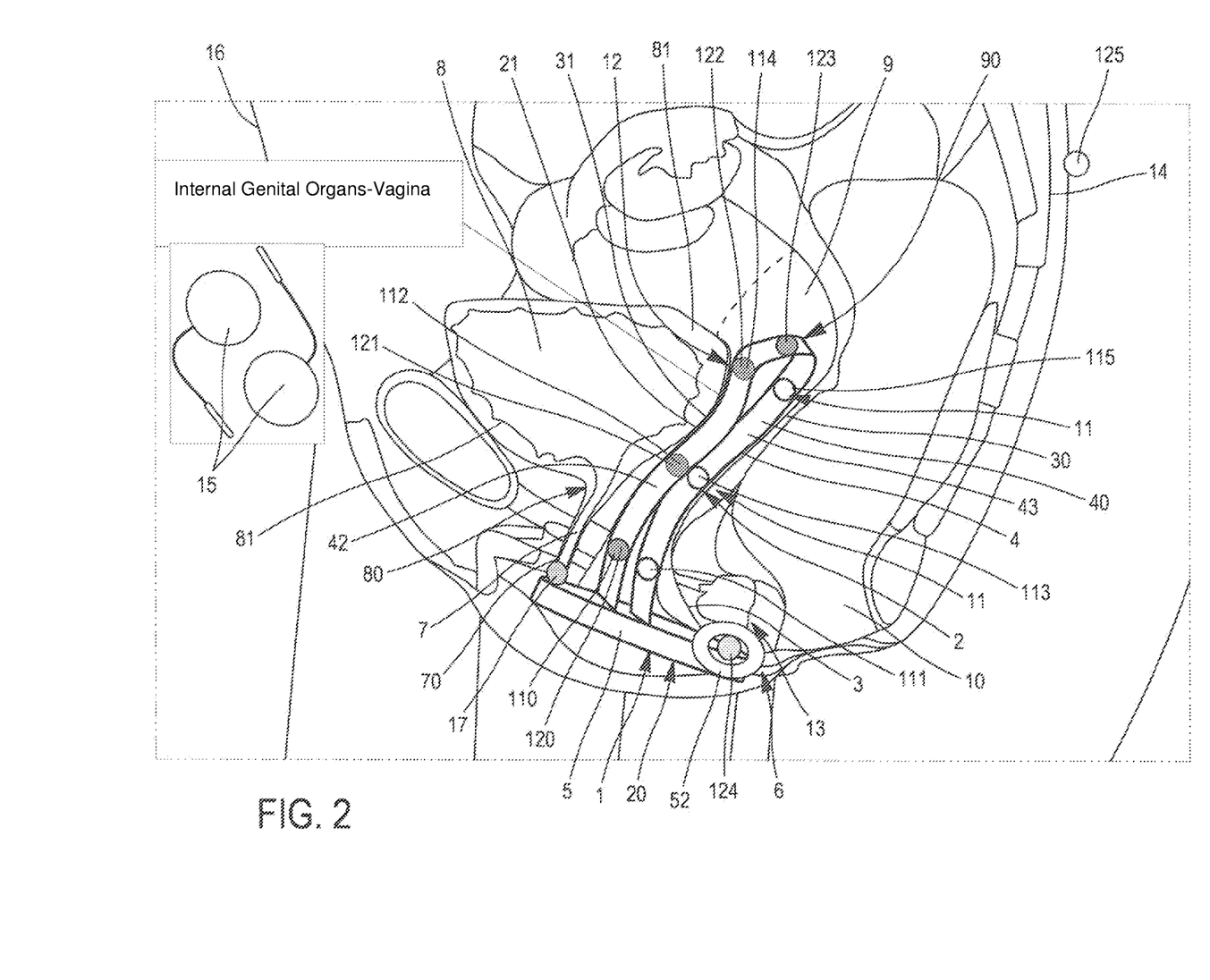
FIG. 2 is a schematic view of the diagnostic probe of FIG. 1, the diagnostic probe being inserted into an endo-vaginal cavity.

Further features and advantages of the invention will become evident from the following detailed description of a non-restrictive exemplary embodiment of the invention, with reference to the accompanying FIGS. 1 and 2.

DETAILED DESCRIPTION OF THE INVENTION

As shown in FIG. 1, the present invention relates to an endo-cavitary diagnostic probe 1, in other words intended to be inserted into a body cavity of a patient, more often of a female patient.

The diagnostic probe 1 according to the invention can thus be inserted into the endo-vaginal cavity 2 of a female patient, in this case it is an "endo-vaginal" probe, or into the rectal cavity and, in this case, it is a so-called "endorectal" probe. In the continuation of the detailed description, the word endo-cavity denotes indifferently an endo-vaginal cavity 2 and an endorectal cavity.

In the exemplary embodiment illustrated in FIGS. 1 and 2, the diagnostic probe 1 is inserted into an endo-vaginal cavity 2 and permits to measure the displacement and the mechanical deformation of the walls 3 of the endo-vaginal cavity 2.

In order to avoid modifying the displacement and/or the mechanical deformation of the walls 3 of the endo-cavity, the diagnostic probe 1 includes a deformable flexible endo-cavitary body 4, which does not offer resistance to deformation.

Advantageously, once it has been inserted into the endo-cavity, for example by means of gynecological forceps, the endo-cavitary body 4 perfectly matches the walls 3 of the endo-cavity.

To this end, the endo-cavitary body 4 is formed by a flexible strip 40 folded in half so as to form a top curve 41, which matches, in a sagittal plane, the walls 3 of said endo-cavity.

The term "sagittal plane" is used to denote the median plane that separates the right half from the left half of the human body. In reality, the median plane is one of the innumerable sagittal planes, the latter being all parallel to the said median planes.

Thus, in the present example, the portion of the flexible strip 40 that is into contact with the anterior endo-cavitary wall 30 of the endo-cavity can be qualified as the anterior part 42 of the endo-cavitary body 4. In the same way, the portion of the flexible strip 40 into contact with the posterior endo-cavitary wall 31 of the endo-cavity can be qualified as the posterior portion 43 of the endo-cavitary body. The anterior 42 and posterior 43 portions of the flexible strip 40 are connected to each other at the top by the top curve 41 of the flexible strip 40.

Preferably, this flexible strip 40 is formed of a flexible polycarbonate printed circuit. Advantageously, the use of a flexible strip 40 made of polycarbonate permits to provide the endo-cavitary body 4 with electronic devices such as physicochemical data sensors.

As illustrated in FIGS. 1 and 2, the endo-cavitary body 4 includes two ends, an anterior end 44 connected to an anterior portion 50 of an ex-vivo base 5, and a posterior end 45 connected to a posterior portion 51 of the base 5 Thus, when the diagnostic probe 1 is inserted into an endo-cavity, the base 5 is arranged at the opening 20 of the endo-cavity. Here, the diagnostic probe 1 is inserted into the endo-vaginal cavity 2 of a female patient, the base 5 being arranged at the commissure of the labia majora (illustrated in FIG. 2).

Advantageously, the base 5 includes a coding that permits to insert the diagnostic probe 1 into the endo-cavity in the sagittal plane so that the anterior portion 42 of the endo-cavitary body 4 is arranged in a sagittal plane against the anterior wall 30 of the endo-cavity, and conversely that the posterior portion 43 of the endo-cavitary body 4 is arranged against the posterior wall 31 of the endo-cavity, always in a sagittal plane.

In addition, the base 5 includes a biocompatible adhesive means 52 that attaches to the skin of the male or female patient so as to secure the maintaining in position of the diagnostic probe 1 inside the endo-cavity. Preferably, the biocompatible adhesive means 52 is positioned at the level of the recto-genital space 6.

As indicated above, the aim of the diagnostic probe 1 of the invention is to measure, in response to an increase in intra-abdominal pressure, the displacement and the mechanical deformation of the endo-cavity and of the surrounding organs, but also the displacement and the deformation of the muscles of the perineum. Advantageously, these measurements permit to accurately and reliably diagnose the causes of the urinary or fecal incontinence.

Indeed, following for example a pregnancy, a childbirth, hormonal changes or also aging, dysfunctions may occur for example at the level of the muscles of the pelvic floor, i.e. the muscles of the perineum. The muscles of the perineum act as a support for numerous organs, including the urethra 7, the bladder 8, the vagina 21 and the uterus 9 in women, or also the rectum 10.

However, the muscles of the perineum are not the only anatomical structures that can be responsible for the urinary or fecal incontinence. As mentioned above, incontinence may also be due to a dysfunction of the urethral or rectal sphincter muscles, the pubo-vaginal or pubo-rectal muscles, or also to ligament weakness causing an organ loosening referred to as "prolapse", as a consequence of an increase in intra-abdominal pressure. Indeed, a urinary or fecal incontinence may be due to ligament weakness causing a prolapse of the urethra 7, the uterus 9, the vagina 21, the rectum 10, or the bladder 8.

In addition, fecal or urinary incontinence is defined as an involuntary loss of urine via the urethra 7, due to physical exertion (coughing, sneezing, laughing, etc.), and without the sensation of a need felt beforehand.

Thus, a diagnosis of the incontinence disorders, established in a reliable manner, subsequently permits to propose an optimized re-education and/or an optimized treatment meeting the specific needs of the patient suffering from incontinence disorders.

As illustrated in FIGS. 1 and 2, in order to identify the anatomical structure or structures responsible for the incontinence disorders of a male or female patient, said diagnostic probe 1 includes at least two pressure sensors 11 arranged on the endo-cavitary body 4 and adapted to measure the pressures at the level of the walls 3 of the endo-cavity, here the endo-vaginal cavity 2.

According to an exemplary embodiment, these pressure sensors 11 are piezoelectric sensors. However, said pressure sensors 11 of the diagnostic probe 1 can be of any type, provided they are capable of permitting to measure a pressure force.

Said pressure sensors 11 are located in the same plane, and all act either in an identical direction or in two opposite directions.

To this end, in the present example, the pressure sensors 11 are arranged on the anterior 42 and posterior portion 43, respectively, of the endo-cavitary body 4. Due to their arrangement on the endo-cavitary body 4 of the probe 1, once the endo-cavitary body 4 of the probe 1 is inserted into the endo-cavity of the patient, the pressure sensors 11 are positioned in a sagittal plane.

Preferably, the diagnostic probe 1 of the invention includes a number higher than two pressure sensors 11 and, yet more preferably, said probe 1 is provided with six pressure sensors 11.

As illustrated in the attached figures, the pressure sensors 11 are arranged pairwise, two by two, in the same plane of an outer plane 40A or inner plane 40B of the flexible strip 40. In the figures, on the outer plane 40A, a first pressure sensor 11 is arranged on the anterior portion 42 of the endo-cavitary body 4 and a second pressure sensor 11 on the posterior portion 43 of the endo-cavitary body 4. Preferably, each pair of pressure sensors 11 acts in opposite directions.

In this way, each pair of pressure sensors 11 is arranged at different levels on the endo-cavitary body 4. Thus, when the endo-cavitary body 4 is inserted into an endo-cavity, here the endo-vaginal cavity 2, each pair of pressure sensors 11 is positioned at various levels of depth in the endo-vaginal cavity 2. Consequently, it is possible to measure the antero-posterior pressures, which are exerted at several levels of the endo-cavity.

As illustrated in FIGS. 1 and 2, the endo-cavitary body 4 includes a first pair of pressure sensors 11, each sensor 11 of which is arranged proximally to the base 5. The first pair of pressure sensors 11 is comprised of a proximal anterior sensor 110 of the base 5 arranged on the anterior portion 42 of the endo-cavitary body 4 and a proximal posterior sensor 111 of the base 5 arranged on the posterior portion 43 of the endo-cavitary body 4.

In the example illustrated in FIG. 2, when the endo-cavitary body 4 is inserted into an endo-vaginal cavity 2, the plurality of pressure sensors 11, 110, 111, 112, 113, 114, 115 is comprised of a proximal anterior pressure sensor 110 and a proximal posterior pressure sensor 111 located at the level where the wall 3 of the endo-vaginal cavity 2 is into contact with the pubo-vaginal and pubo-rectal muscles. Thus, this first pair of pressure sensors 110, 111 permits, in response to an increase in intra-abdominal pressure, to indirectly measure the antero-posterior pressure the pubo-vaginal and pubo-rectal muscles exert on the walls 3 of the endo-vaginal cavity 2.

The endo-cavitary body 4 includes the plurality of pressure sensors 11 being comprised of a second pair of pressure sensors 112, 113 (an intermediate proximal anterior pressure sensor 112 and an intermediate proximal posterior pressure sensor 113) arranged at an intermediate position 46 (an anterior intermediate position 46A, a posterior intermediate position 46B) between the base 5 and the top loop 41 of the flexible strip 40.

The second pair of pressure sensors 11 is comprised of an intermediate anterior sensor 112 arranged on the anterior portion 42 of the endo-cavitary body 4 and an intermediate posterior sensor 113 arranged on the posterior portion 43 of the endo-cavitary body 4.

In the example illustrated in FIG. 2, once the endo-cavitary body 4 is inserted into the endo-vaginal cavity 2, the intermediate anterior pressure sensor 112 is located in an area where the wall 3 of the endo-vaginal cavity 2 is into contact with the junction of the bladder neck (JUV) 80, while the intermediate posterior pressure sensor 113 is located in an area where the wall 3 of the endo-vaginal cavity 2 is into contact with the rectum 10.

Thus, the second pair of pressure sensors 11 permits to measure the antero-posterior pressures the bladder neck 80 and the rectum 10 apply onto the wall 3 of the endo-vaginal cavity 2.

The endo-cavitary body 4 includes a third pair of pressure sensors 11 arranged on the flexible strip 40 proximally to the top curve 41 of the flexible strip 40.

The third pair of pressure sensors 11 is comprised of a top proximal anterior sensor 114 arranged on the anterior portion 42 of the endo-cavitary body 4 and a top proximal posterior sensor 115 arranged on the posterior portion 43 of the endo-cavitary body 4.

As illustrated in FIG. 2, when the endo-cavitary body 4 is inserted into the endo-vaginal cavity 2, the top proximal anterior pressure sensor 114 is located in an area where the wall 3 of the endo-vaginal cavity 2 is into contact with the bladder dome 81, i.e. of the upper portion of the bladder 8. Conversely, once the endo-cavitary body 4 is inserted into the endo-vaginal cavity 2, the top proximal posterior pressure sensor 115 is located in an area where the wall 3 of the endo-vaginal cavity 2 is into contact with the rectum 10. Thus, the third pair of pressure sensors 11 permits to measure the antero-posterior pressure the bladder dome 81 and the rectum 10 exert onto the wall 3 of the endo-vaginal cavity 2.

In addition, in order to measure the displacement and the deformation of the endo-cavity and the surrounding organs, but also the displacement and the deformation of the muscles of the perineum, the whole due to an increase in the intra-abdominal pressure, the probe 1 also includes at least one means 12 for measuring the displacement of the anatomical structures along the three axes X, Y and Z, i.e. a measurement of the displacement and the deformation of the anatomical structures in three dimensions or "3D".

In the example illustrated in FIGS. 1 and 2, the probe includes at least four means 12 for measuring the displacement of the anatomical structures, which are arranged at different levels of depth when the probe 1 is inserted into an endo-cavity.

The means for measuring in 3D the displacement 12, 120, 121, 122, 123, 124 of the endo-cavitary wall 3 may be formed by an inertial unit 12A.

More specifically, an inertial unit 12A corresponds to a device incorporating both acceleration and angular velocity sensors, for example three gyrometers and three accelerometers. This inertial unit 12A device permits to calculate, in real time, based on the components of the acceleration, the evolution of the velocity vector and the position of the assembly, here the diagnostic probe 1 of the invention, at the level of which said inertial unit 12A is positioned.

However, the means 12 for measuring the displacement may also be formed by any other means adapted to carry out such a measurement of displacement and acceleration along the three axes X, Y, Z.

Thus, in order to measure the displacement of the anatomical structures surrounding the endo-cavity, which the probe 1 is inserted into, the endo-cavitary body 4 is provided with four displacement means 12 adapted to measure the displacement of the walls 3 of the endo-cavity at four different levels of depth.

To this end, the endo-cavitary body 4 includes a first means 120 for measuring the displacement arranged on the flexible strip 40 proximally to the base 5. In the present example, once the endo-cavitary body 4 is inserted into the endo-vaginal cavity 2, the first means for measuring 120 the displacement is located at the level where the wall 3 of the endo-vaginal cavity 2 is into contact with the pubo-vaginal and pubo-rectal muscles (illustrated in FIG. 2). Thus, the first means for measuring 120 the displacement permits, in response to an increase in the intra-abdominal pressure, to indirectly measure the displacement and the deformation of the pubo-vaginal and pubo-rectal muscles by measuring the displacement and the deformation of the wall 3 of the endo-vaginal cavity 2.

The endo-cavitary body 4 includes a second means for measuring 121 the displacement arranged at an intermediate position between the base 5 and the top loop 41 of the flexible strip 40. Here, when the endo-cavitary body 4 is inserted into the endo-vaginal cavity 2, the second means for measuring 121 the displacement is located at the level where the wall 3 of the endo-vaginal cavity 2 is into contact with the junction of the bladder neck 80 (illustrated in FIG. 2). Thus, the second means for measuring 121 the displacement permits, in response to an increase in the intra-abdominal pressure, to indirectly measure the displacement and the deformation of the junction of the bladder neck 80 by measuring the displacement and the deformation of the wall 3 of the endo-vaginal cavity 2.

The endo-cavitary body 4 includes a third means for measuring 122 the displacement arranged on the flexible strip 40 near the top curve 41. Thus, when the endo-cavitary body 4 is inserted into an endo-vaginal cavity 2, the third means for measuring 122 the displacement is located at the level where the wall 3 of the endo-vaginal cavity 2 is into contact with the bladder dome 81 (illustrated in FIG. 2). Consequently, the third means for measuring 122 the displacement permits, in response to an increase in the intra-abdominal pressure, to indirectly measure the displacement and the deformation of the bladder dome 81 by measuring the displacement and the deformation of the wall 3 of the endo-vaginal cavity 2. This third means for measuring 122 the displacement permits inter alia to identify a prolapse of the bladder 8.

The endo-cavitary body 4 includes a fourth means for measuring 123 the displacement arranged at the top of the top curve 41 of the flexible strip 40. Here, when the endo-cavitary body 4 is inserted into the endo-vaginal cavity 2, the fourth means for measuring 123 the displacement is located at the level of a zone of the wall 3 of the endo-vaginal cavity 2 that is into contact with the neck 90 of the uterus 9 (illustrated in FIG. 2). Therefore, the fourth means for measuring 123 the displacement permits, in response to an increase in the intra-abdominal pressure, to indirectly measure the displacement and the deformation of the neck 90 of the uterus 9 by measuring the displacement and the deformation of the wall 3 of the endo-vaginal cavity 2. Thus, this fourth means for measuring 123 the displacement permits namely to measure and identify a prolapse of the uterus 9.

In addition, according to a peculiarity of the present embodiment illustrated in FIGS. 1 and 2, the first 120, second 121 and third 122 means for measuring the displacement are arranged, on the one hand, on the anterior portion 42 of the endo-cavitary body 4 and, on the other hand, respectively, in the immediate vicinity of the pressure sensors 110, 112, 114.

Since the diagnostic probe 1 is inserted at the level of an endo-cavity, the means for measuring 12 the displacement therefore permit to measure the displacement and the deformation of the endo-cavitary wall 3, and thus an indirect measurement of the displacement and the deformation of the anatomical structures surrounding this endo-cavity, namely the pubo-vaginal/pubo-rectal muscles, the bladder 8, the sphincters located at the junction of the bladder neck 80, the prostate or the uterus 9, etc.

Moreover, in order to measure the displacement of the muscles of the perineum in response to an increase in the intra-abdominal pressure, the diagnostic probe 1 includes a fifth means for measuring 124 the displacement, which is arranged on the base side 53 of base 5 so as to be pressed against the tendinous units 13 of the perineum at the level of the recto-genital ring. In this way, it can be considered to evaluate the displacement of the muscles of the perineum in all directions, in other words from top to bottom, from front to back, and laterally.

Advantageously, in the present example, the biocompatible adhesive means 52 is arranged around the fifth means for measuring 124 the displacement. This feature permits to ensure a permanent contact between the fifth means for measuring 124 the displacement and the recto-genital ring. In addition, this fifth means for measuring 124 the displacement also constitutes a spatial reference element X, Y, Z for the means for measuring 120, 121, 122, 123 the displacement, which are located on the endo-cavitary body 4.

In the example illustrated in FIG. 2, in order to record the global movements of the pelvis during an increase in the intra-abdominal pressure and thus to constitute, in the event of a movement of the patient's body, a spatial reference element X, Y, Z, for the other means for measuring 120, 121, 122, 123, 124 the displacement, the diagnostic probe 1 is connected to a sixth means for measuring 125 the displacement.

This sixth means for measuring 125 the displacement is positioned on the body of the male or female patient, preferably at the level of the sacrum 14. This sixth means for measuring 125 the displacement permits to avoid, in the event of inadvertent or voluntary movement, carried out by the patient during the examination, to distort the measurements of displacement of the wall 3 of the endo-vaginal cavity 2, of the organs surrounding the vagina 21 and of the muscles of the perineum. Indeed, in order to perform a diagnosis of incontinence, the patient will generally be asked, for example, to cough, in order to obtain a measurement in a situation of physical exertion, which is likely to result namely in stress urinary incontinence.

More precisely, stress urinary incontinence, which corresponds to the dysfunction of closing of the muscles of the urethra 7, of the muscles of the perineum, and of the ligaments keeping the organs of the abdominal cavity in position.

Indeed, these anatomical structures, when they are functional, permit to withstand an increase in the abdominal pressure, due to a situation of stress, such as an attack of coughing, laughing, sneezing, or a physical exercise.

In case of a dysfunction of closing of the muscles of the urethra 7, of the muscles of the perineum and of the ligaments supporting the organs of the abdominal cavity, the pressure increases in the abdominal cavity namely due to an effort, this pressure has a repercussion on the bladder 8 and a urine leakage may occur.

In order to detect the starting point of the increase in intra-abdominal pressure over time, the probe 1 is connected to two electromyographic electrodes 125A as the sixth means for measuring displacement arranged on the abdomen of the male or female patient. These electromyographic electrodes 125A are adapted to record the abdominal electromyographic activity, which is at the origin of the increase in the intra-abdominal pressure.

In addition, in order to detect, as a result of an intra-abdominal increase, the time at which urine leakage occurs, the ex-vivo base 5 includes at least one urine detector 17 adapted to be brought into contact with the urethral orifice 70, the urinary meatus. In the example illustrated in FIG. 2, the urine detector 17 is arranged at the level of the anterior portion of the vulva of the patient.

According to an additional feature not shown of the invention, for hygienic reasons during its insertion into a body cavity, the diagnostic probe 1 is provided with a disposable sheath 4A covering the endo-cavitary body 4. The sheath 4A may be made of a biocompatible polymeric material, for example of silicone.

In order to increase the maintaining of the diagnostic probe 1 within the endo-cavity during the examination, the sheath may comprise, on its external surface, a holding means cooperating with the walls 3 of the endo-cavity so as to ensure that the probe 1 is maintained in position during the examination. These holding means may be formed by a temporary organic adhesive or a particular structure of the outer surface of the sheath, which would have the effect of increasing the coefficient of friction of the outer surface of the sheath with the wall 3 of the endo-cavity.

Advantageously, the features of the probe permit to measure, in real time, when the patient is in a situation of stress, the starting point of the increase in intra-abdominal pressure defining the origin of the measurements according to the moment, the antero-posterior pressures that are applied to the endo-cavity, the deformation and the displacement of the organs surrounding the endo-cavity, the deformation and the displacement of the muscles of the perineum, and the time when urinary leakage occurs.

All these parameters permit to measure the response time of the myotatic reflex of all the structures relative to the origin of the increase in the intra-abdominal pressure. It is thus possible to have information on the quality of the myotatic reflex of these anatomical structures and namely of the pubo-vaginal, the pubo-rectal muscles, of the urethral and anal sphincters, and of the muscles of the perineum.

In addition, the diagnostic probe 1 according to the invention cooperates with data processing means 126 in communication with the pressure sensors 11 and means for measuring displacement 12, which are adapted to plot the acceleration and deformation amplitude curves of the endo-cavitary wall 3 along the three axes (X, Y and Z), i.e. of the three-dimensional or "3D" curves. Each means for measuring 12 the displacement of the probe 1 generates data, which permit to draw a curve of acceleration and of 3D movement amplitude specific to the zone of the wall 3 of the endo-cavity, which it is placed into contact with.

These curves will also permit to determine the amplitude of the displacement of the anatomical structures at the level of each measuring means 12, and the level of acceleration at which the myotatic reflex of these anatomical structures occurs. It is thus possible to follow the evolution of the deformation and the displacement of these anatomical structures according to a time scale taking as origin the starting point of the increase in the intra-abdominal pressure recorded by the electromyographic electrodes 15.

The data processing means are also adapted to correlate the displacement and deformation curves with the antero-posterior pressure data recorded by the pressure sensors 12 and which are exerted on the walls 3 of the body cavity.

In addition, by integrating all the parameters measured by the diagnostic probe 1, the data processing means are adapted to model a dynamic three-dimensional view of the displacement and the deformation of the endo-cavity from the origin of the increase in the intra-abdominal pressure recorded by the electromyographic electrodes 15. This modeling permits to then visualize the deformation and the displacement of the endo-cavity as well as the deformation and the displacement of the muscles of the perineum.

Thus, it is possible to accurately determine the time at which the myotatic reflex of each anatomical structure occurs, the time at which the urine or fecal leakage occurs, the level of resistance at which the urinary leakage occurs and the anatomical structure that is responsible for this urinary or fecal leakage and, hence, the anatomical structure that is responsible for incontinence.

The invention thus permits to perform accurate measurements of the behavior of the anatomical structures related to the mechanism of continence, so as to establish the diagnosis of the dysfunctions affecting these anatomical structures responsible for the urinary or fecal incontinence.

The patient is then referred to a suitable treatment and/or re-education in a very accurate manner, thanks to the diagnosis, which has been obtained by means of the present diagnostic probe 1.

I claim:

1. A diagnostic probe for being inserted into an endo-cavity having walls and a muscle, the diagnostic probe comprising:
    a base having an anterior portion and a posterior portion opposite said anterior portion with a base side between said anterior portion and said posterior portion; and
    an endo-cavitary body being comprised of a flexible strip having an outer plane and an inner plane so as to oppose the walls of the endo-cavity without resistance,
    wherein said flexible strip is comprised of an anterior end connected to said anterior portion of said base and a posterior end connected to said posterior portion of said base so as to form a top curve halfway between said anterior end and said posterior end and in a sagittal plane so as to align said top curve with the walls of said endo-cavity,
    wherein the flexible strip forms an anterior part between said anterior end and said top curve so as to align said flexible strip with an anterior wall of said endo-cavity, and an anterior intermediate position halfway between said posterior end and said top curve, and
    wherein said flexible strip forms a posterior part between said posterior end and said top curve so as to align said flexible strip with a posterior wall of said endo-cavity, and a posterior intermediate position halfway between said posterior end and said top curve;
    a plurality of pressure sensors arranged on said outer plane of said flexible strip, wherein said plurality of pressure sensors is comprised of a proximal anterior pressure sensor between said anterior end and said anterior intermediate position and a proximal posterior pressure sensor between said posterior end and said posterior intermediate position;
means for measuring displacement on said flexible strip; and
a special reference element on said base side of said base.

2. The diagnostic probe, according to claim 1, further comprising:
a data processing means in communication with said plurality of pressure sensors, said means for measuring displacement and said spatial reference element so as to reconstruct a dynamic three-dimensional view of the endo-cavity.

3. The diagnostic probe, according to claim 1, further comprising: a biocompatible adhesive means placed on said base side of base so as to reinforce position of said base.

4. The diagnostic probe, according to claim 1, further comprising: a urine detector on said base side of said base.

5. The diagnostic probe, according to claim 1, wherein said means for measuring displacement comprises an inertial unit.

6. The diagnostic probe, according to claim 1, wherein said spatial reference element is further comprised of an inertial unit so as to measure displacement of a tendon unit of a perineum and a sacrum.

7. The diagnostic probe, according to claim 1, further comprising: at least two electrodes in communication with said pressure sensors and said means for measuring displacement so as to measure abdominal electromyographic activity.

8. The diagnostic probe, according to claim 1, wherein said means for measuring displacement comprises a first means for measuring displacement adjacent said anterior end, a second means for measuring displacement at said anterior intermediate position, a third means for measuring displacement between said anterior intermediate position and said top curve, and a fourth means for measuring displacement at said top curve.

9. The diagnostic probe, according to claim 1, wherein said plurality of pressure sensors is further comprises of an intermediate anterior pressure sensor at said anterior intermediate position, a top proximal anterior pressure sensor between said anterior intermediate position and said top curve, a top proximal posterior pressure sensor between said posterior intermediate position and said top curve, and an intermediate posterior pressure sensor at said posterior intermediate position.

10. The diagnostic probe, according to claim 1, further comprising: a sheath being comprised of biocompatible polymeric material and covering said endo-cavitary body.

* * * * *